(12) United States Patent
Olgiati et al.

(10) Patent No.: US 10,213,320 B2
(45) Date of Patent: Feb. 26, 2019

(54) SURGICAL GUIDE FOR IMPLANTING A KNEE PROSTHESIS

(75) Inventors: Gianluca Olgiati, Como (IT); Massimiliano Bernardoni, Figino (CH); Francesco Siccardi, Sonvico (CH); Alberto Siccardi, Sonvico (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 1045 days.

(21) Appl. No.: 14/241,297

(22) PCT Filed: May 16, 2012

(86) PCT No.: PCT/IB2012/000958
§ 371 (c)(1),
(2), (4) Date: Apr. 30, 2014

(87) PCT Pub. No.: WO2012/156806
PCT Pub. Date: Nov. 22, 2012

(65) Prior Publication Data
US 2014/0236305 A1    Aug. 21, 2014

(30) Foreign Application Priority Data
May 17, 2011    (CH) ...................................... 0835/11

(51) Int. Cl.
*A61B 17/90*    (2006.01)
*A61F 2/46*    (2006.01)
(Continued)

(52) U.S. Cl.
CPC ............ *A61F 2/461* (2013.01); *A61B 17/155* (2013.01); *A61B 17/1764* (2013.01); *A61F 2/38* (2013.01); *A61B 2017/568* (2013.01)

(58) Field of Classification Search
CPC ...... A61B 17/15; A61B 17/151; A61B 17/154; A61B 17/155; A61B 17/157;
(Continued)

(56) References Cited

U.S. PATENT DOCUMENTS

| 4,959,066 A | 9/1990 | Dunn et al. |
| 5,312,411 A | 5/1994 | Steele et al. |

(Continued)

FOREIGN PATENT DOCUMENTS

| EP | 0979636 | 2/2000 |
| WO | 2007097854 | 8/2007 |

(Continued)

*Primary Examiner* — Zade Coley
*Assistant Examiner* — Jessica Weiss
(74) *Attorney, Agent, or Firm* — Allen, Dyer, Doppelt + Gilchrist, P.A.

(57) ABSTRACT

The invention relates to a surgical guide (1, 1') for implanting a knee prosthesis, advantageously capable of allowing the intraoperative balancing of the knee ligaments, comprising: a first component (G1, G1') intended for uniquely coupling with the distal epiphyseal end (Ed) of a femur (Fe); a template (Gr, Gr') rotatably mounted with respect to said first component (G1, G1') and intended for guiding a marking operation of said distal epiphyseal end (Ed) aimed to determine the position of a knee prosthesis to be implanted; and a second component (G2) intended for solidly coupling said template (Gr, Gr') with a proximal epiphyseal end (Ep) of a tibia (Ti) corresponding to said femur (Fe).

24 Claims, 10 Drawing Sheets

(51) Int. Cl.
  *A61B 17/15* (2006.01)
  *A61B 17/17* (2006.01)
  *A61F 2/38* (2006.01)
  *A61B 17/56* (2006.01)

(58) Field of Classification Search
  CPC ..... A61B 17/1764; A61B 17/568; A61F 2/38;
  A61F 2/461
  USPC .................................. 606/86 R, 87–90, 96–98
  See application file for complete search history.

(56) References Cited

U.S. PATENT DOCUMENTS

| | | | |
|---|---|---|---|
| 5,597,379 A * | 1/1997 | Haines | A61B 17/1764 606/80 |
| 5,607,431 A | 3/1997 | Dudasik et al. | |
| 5,683,397 A | 11/1997 | Vendrely et al. | |
| 5,702,460 A | 12/1997 | Carls et al. | |
| 5,743,909 A | 4/1998 | Collette | |
| 5,860,980 A * | 1/1999 | Axelson, Jr. | A61B 17/155 606/88 |
| 5,916,219 A | 6/1999 | Matsuno et al. | |
| 6,193,724 B1 | 2/2001 | Chan | |
| 6,554,837 B1 | 4/2003 | Hauri et al. | |
| 7,534,263 B2 | 5/2009 | Burdulis et al. | |
| 7,572,262 B1 * | 8/2009 | Hoeppner | A61B 17/155 606/87 |
| 7,582,091 B2 | 9/2009 | Duncan et al. | |
| 8,632,547 B2 | 1/2014 | Maxxson et al. | |
| 2003/0018338 A1 | 1/2003 | Axelson, Jr. et al. | |
| 2004/0039395 A1 | 2/2004 | Coon et al. | |
| 2004/0102785 A1 | 5/2004 | Hodorek et al. | |
| 2005/0020941 A1 | 1/2005 | Tarabichi | |
| 2005/0070897 A1 | 3/2005 | Petersen | |
| 2005/0075632 A1 | 4/2005 | Russell et al. | |
| 2005/0171545 A1 | 8/2005 | Walsh et al. | |
| 2005/0177169 A1 | 8/2005 | Fisher et al. | |
| 2005/0245934 A1 | 11/2005 | Tuke et al. | |
| 2006/0122617 A1 | 6/2006 | Lavallee et al. | |
| 2006/0195111 A1 | 8/2006 | Couture | |
| 2006/0271056 A1 | 11/2006 | Terrill-Grisoni et al. | |
| 2010/0160919 A1 * | 6/2010 | Axelson, Jr. | A61B 17/155 606/89 |
| 2010/0217338 A1 * | 8/2010 | Carroll | A61B 17/155 606/86 R |
| 2011/0245835 A1 | 10/2011 | Dodds et al. | |
| 2012/0209275 A1 * | 8/2012 | Fox | A61B 17/157 606/88 |
| 2012/0277751 A1 * | 11/2012 | Catanzarite | A61B 17/155 606/88 |
| 2013/0289570 A1 | 10/2013 | Chao | |
| 2015/0173774 A1 * | 6/2015 | Leslie | A61B 17/155 606/102 |

FOREIGN PATENT DOCUMENTS

| | | | |
|---|---|---|---|
| WO | 2009045960 | 4/2009 | |
| WO | WO 2011/141722 | * 11/2011 | ............. A61B 17/15 |

\* cited by examiner

SURGICAL GUIDE FOR IMPLANTING A KNEE PROSTHESIS

FIELD OF APPLICATION

The present invention relates to a surgical guide for implanting a knee prosthesis, and in particular to, a guide designed for the intraoperative alignment and balancing of the knee ligaments.

BACKGROUND

Surgical guides, from the most rudimentary ones to the most sophisticated, for assisting the operation of replacement the knee joint, are described in the literature and are also widely used in a wide range of daily applications. It is also known that the position of the bony resections must be defined based on the patient's ligament balance to allow a correct functional recovery of the joint. The tibial resection is used to this end as a reference for defining the outer rotation of the femoral prosthetics component.

The most typical system is that based on the intramedullary canal of the femur but this implies possible complications for the patient in particular due to the greater invasiveness of the equipment to use, as well as to a reduced visibility of the equipment support bone, implying greater difficulty in achieving the required accuracy. The weakness of conventional equipment lies above all in the fact that they are still too invasive and as such they may cause complications for the patient. A strict relation therefore exists between the invasiveness of the equipment (especially if not up-to-date) and the frequency and seriousness of complications for patients. This adds up to the consequent poor visibility of the patient's bone during the positioning of the femoral guide that often impairs the critical aspect of obtaining good results in terms of accuracy and repeatability.

SUMMARY

Generally speaking, a surgical guide is for implanting a knee prosthesis and may include a first component. The first component may comprise at least one attachment portion configured to be fixed to a distal epiphyseal end of a femur, and an arch structure coupled to the at least one attachment portion and comprising a curved arm configured to be adjacent the distal epiphyseal end of the femur, and an appendix arm extending from the curved arm. The surgical guide may comprise a template associated with the first component and configured to guide a marking operation of the distal epiphyseal end to determine a position of the knee prosthesis. The template may be configured to be rotatably mounted relative to the first component, the appendix arm delimiting rotating motion of the template. The surgical guide may also include a second component configured to couple the template with a proximal epiphyseal end of a tibia corresponding to the femur.

DETAILED DESCRIPTION

Figure 1:
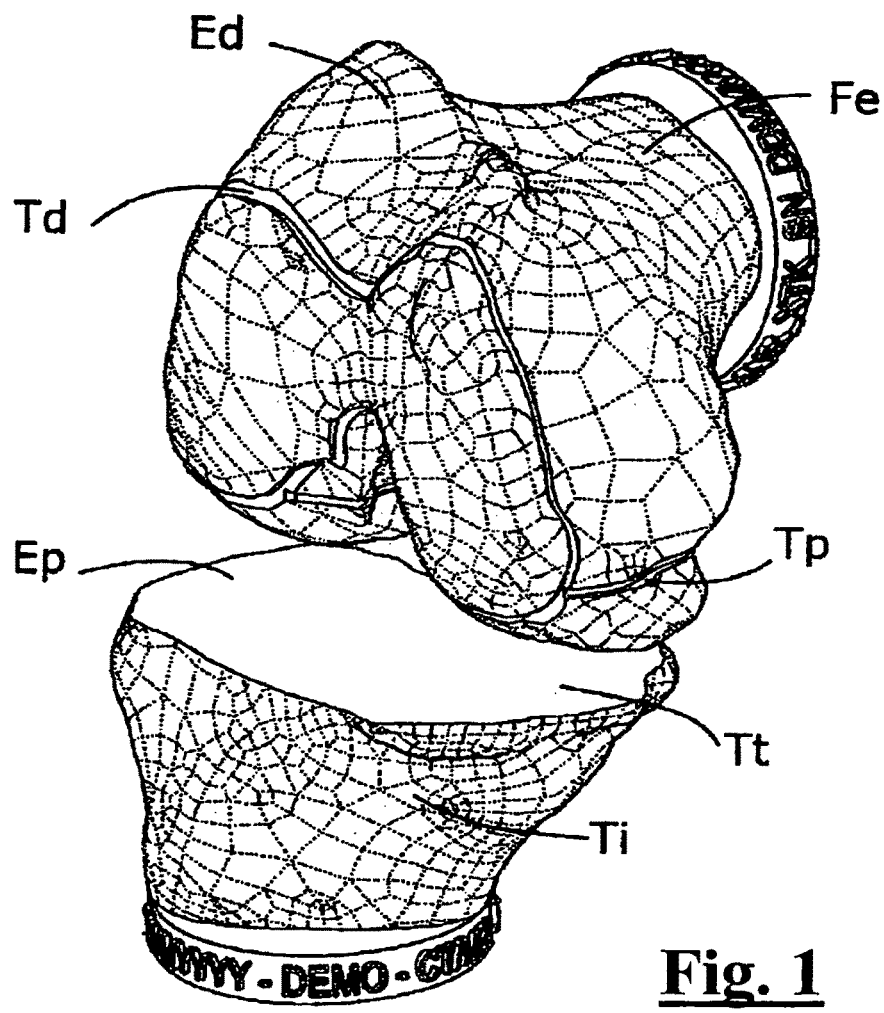
FIG. 1 shows a bony site prepared for coupling with the surgical guide according to the present invention.

The patent literature related to the knee ligaments includes: D1—International Application PCT/US2008/078143, filed on 29 Sep. 2008, published as WO2009/045960, corresponding to EP no. 2194889 (in the name of De Puy); D2—U.S. Pat. No. 7,534,263, filed on 2 Dec. 2004, corresponding to WO2006/060795 and to EP 1833387 (in the name of ConforMIS). D1 describes in a set of a couple of hundreds of pages, 112 drawings and 249 claims, about 200 embodiments of methods and instruments for aligning knee ligaments which use the femur as a support base;

D2 provides some hundreds of bibliographic references related to the use of the patella instead of the femur. D1 refers to a femoral cutting block that allows the operator to inspect whether the positioning of such block has been appropriately made. To this end, in addition to a first per se known guide, the block is also provided with a second guide that extends at the back from the front body and defines a window between the same guides which are provided with a first and a second tab with engagement with the distal front and back surfaces. As mentioned, D2 relates to a specific use of the patella.

In addition to the above D1 and D2, D3—WO2007/097854 (in the name of OTIS MED Corp.) describes cutting guides that engage the front, distal and back surface without having a first and a second tab that form a window between each other and without comprising tabs that define a coplanar blind groove with a guiding slit on the front side.

In conclusion, these and other approaches and the relevant devices used to date certainly have important merits but unfortunately they are not free from drawbacks, such as those that relate to an insufficient mini-invasiveness, the interference of the cutting device with the rotula tendon and an insufficient visibility of the bone. Operative techniques have recently become widespread, which use patient specific surgical guides. These operative techniques envision the acquisition, in the preoperative stage, of CAT images of the patient's bony site. Starting from the bony markers that can be found in such images, a preoperative planning of the operation is carried out and specifically shaped guides are made which adjust to the patient's bone to make the cuts and the holes needed for implanting the knee prosthesis.

Patient specific guides allow most of the above drawbacks to be solved and in particular they are characterized by such accuracy as to ensure a unique positioning and high stability. On the other hand, however, patient specific guides have a drawback due to the strictness of the preoperative planning.

In fact, while CAT images allow seeing the bony markers generally sufficient for a correct planning of the operation, they do not allow the soft tissues to be displayed, in particular the tendons that surround the knee joint. In some cases, the configuration of the planned prosthesis may cause an unbalance of the loads on the tendons, and it should be corrected based on a diagnostic evidence that may only be gathered during the operation. Patient specific guides according to the prior art, however, do not allow the cutting and/or perforation settings planned in the preoperative stage to be modified.

The technical problem at the basis of the present invention is to provide surgical guides for implanting a knee prosthesis that do not have the drawbacks mentioned above, in particular that have such invasiveness as not to cause inconveniences to the patient and that allow the alignment of the resections to the mechanical axis and the intraoperative balancing of the knee ligaments.

Another object is to provide guides that allow the transmission of the force states to be maximized and the interference of the cutting device with the rotula tendon to be minimized. Yet another object is to allow at any step and time the assessment, with the utmost accuracy and with no possibility of gross errors, of the patient's ligament condition and accordingly, the rotation of the relative guide. This and other objects are achieved with the equipment having the peculiar features and aspects cited in the Claims at the bottom of this Description, which should also be considered as incorporated herein as well.

In brief, the guide according to the finding comprises a device that uniquely couples with the distal femoral epiphyseal end and a specially shaped guide, substantially as a horseshoe, for coupling with the proximal tibial epiphyseal end where a resection has already been made for correcting the mechanical axis. If needed, the proximal tibial epiphyseal end may be prepared with an optional cover for favoring the load distribution along the outer profile of the cortical bone.

The device, which in one embodiment thereof appears like a frame coupled with the femoral epiphyseal end, is characterized by a section or portion capable of rotating directly connected to the "horseshoe" guide, hereinafter the to be astride, which acts as transmitter of the ligament state to the template for the outer rotation associated with the support frame.

According to a first aspect of the present disclosure, the distal portion of the frame is associated with a guide characterized in that it can turn on a not too large angle; the rotation is produced by the intermediate piece and allows the outer rotation of the femoral prosthesis to be planned on the basis of the patient's ligament balance. Advantageously, the support frame provides a firm constraint of the femoral guide against any violations of the intramedullary canal while not using it as a reference.

According to another aspect of the present disclosure, the femoral guide object of this invention is also characterized by a distal cutting template capable of shifting in proximal-distal direction for carrying out some corrections on the planned femoral resection. A crucial aspect of the invention is that the femoral guide, designed based on the same anatomy of the single patient, gives such accuracy to the device as to ensure a unique positioning and a high stability.

According to a further aspect of the present disclosure, the guide for the outer rotation can rotate opposing a predetermined torsional resistance to the movement. Such resistance introduces a compensation component on the knee ligament balance that allows a predetermined and controlled joint balance to be obtained allowing the operator to manage and measure the tension of the outer and inner collateral ligament.

In the perspective of FIG. 1 there are shown the distal epiphyseal end Ed of a femur Fe and the proximal end Ep of a tibia Ti of a patient, whereon a total knee prosthesis has to be implanted. As is seen, this latter end Ep is already placed in conditions of modularity with the distal epiphyseal end Ed of femur Fe. Two cutting planes are already indicated on this latter end, in particular a distal cutting plane Td orthogonal to the axis of femur Fe and a back cutting plane Tp parallel to the axis of femur Fe. The cuts defined by the planes, which shall thereafter allow the coupling with the total knee prosthesis, are yet to be made.

Preferably, the epiphyseal end Ep of tibia Ti may be prepared with an optional covering Co (see FIG. 2) or coating layer (even partially covering the surface) for favoring the distribution mainly of the loads along the outer profile of the cortical bone (not shown). The cover Co is preferably made of a metal or thermoplastic material.

Figure 2:
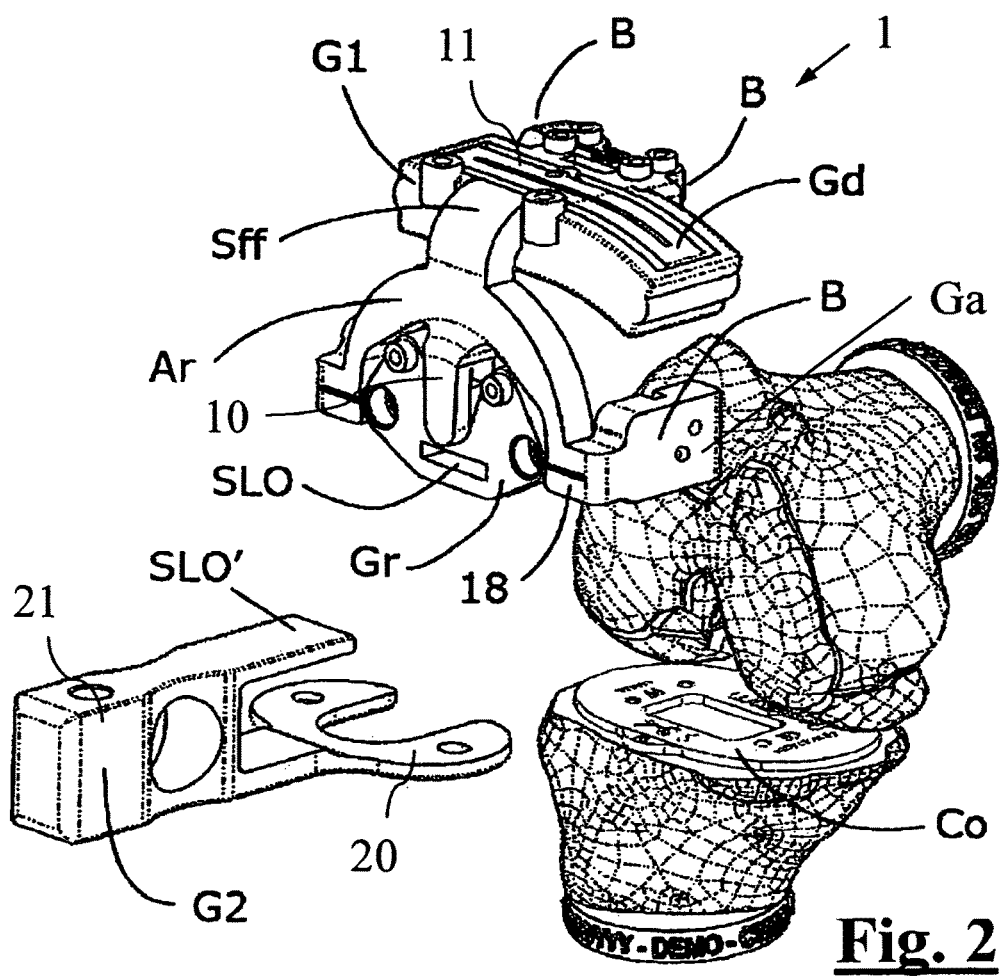
FIGS. 2, 3 and 5 show perspective views of a first embodiment version of the surgical guide according to the present invention, coupled with the bony site of FIG. 1.

The perspective of FIG. 2 shows (along with the bony structure Fe, Ti described above) a first version of the surgical guide 1 according to the invention, consisting of:—a first component G1 associated with femur Fe; and—a second component G2 for adjusting the turning position. The first component G1 consists in a main attachment portion Gd connected by a connection Sff to an arch structure Ar, from the center whereof an appendix 10 protrudes where to a template Gr is attached (FIG. 4) which consists of a polygonal body. The first component G1 is completed by four supports B that couple with shape constraint with femur Fe. Typically, the whole template Gr is coupled with a second "astride" component G2 inserted ad hoc into slot SLO (FIG. 3) obtained under appendix 10. The reference numerals 15, 16, 17 indicate the fixing nails of the surgical guide 1 in the position imposed by the surgeon.

Figure 3:
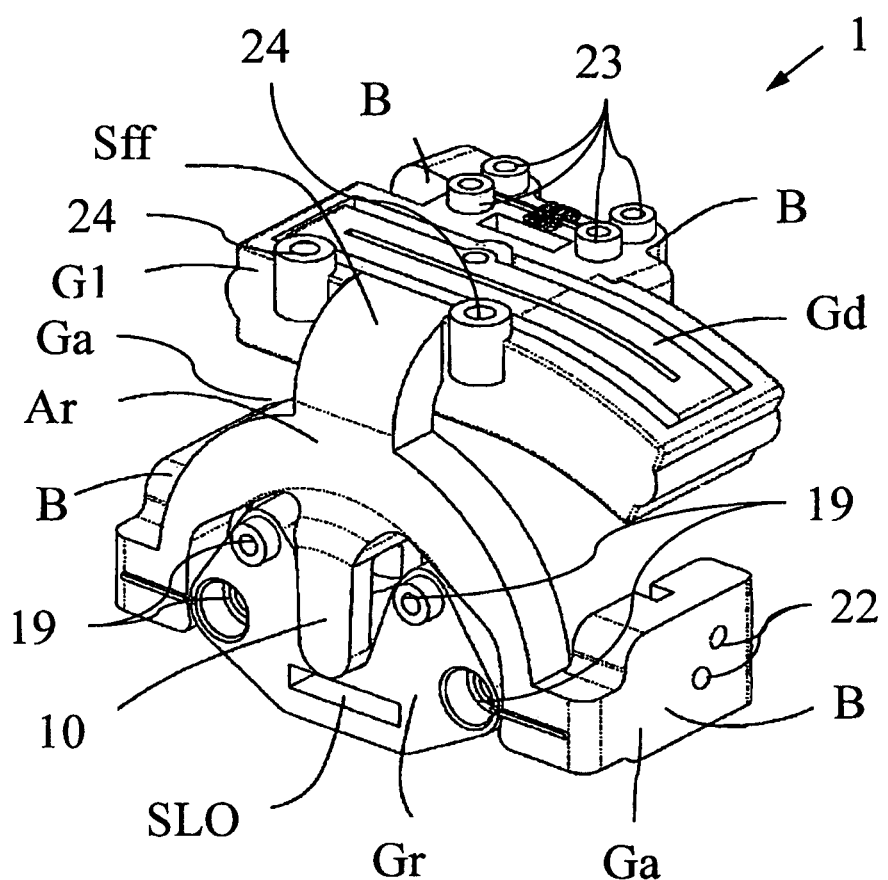

In FIG. 2, the surgical guide 1 is represented not yet coupled with the bony site. FIG. 3 only shows the first component G1. As is seen, the first component G1 respectively consists of: the main attachment portion Gd connected to the arch structure Ar through connection Sff; the arch structure Ar supports template Gr through an appendix 10 (FIG. 3) hinged on pin 12; the above components constitute the portion of surgical guide 1 that couples with the distal end Ed of femur Fe through the four supports B with shape constraint.

Figure 4:
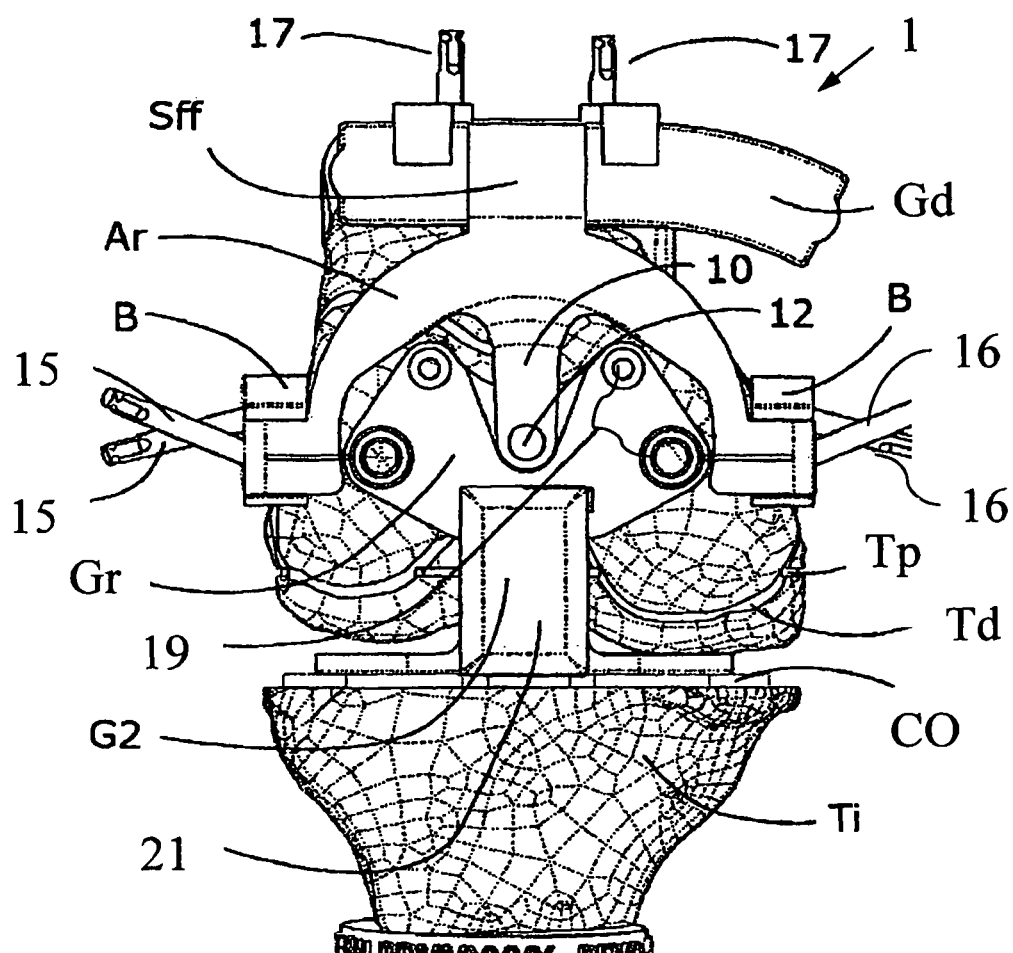
FIG. 4 shows a front view of the assembly of FIG. 5.

FIG. 4 shows the front view of the equipment in use, positioned on the patient's bones. The polygonal geometry imparted to template Gr articulated about pin 12 is clearly visible in the FIG. 4. The fixing nails 15, 16 and 17 are also clearly visible; a dual line 18 (FIG. 2) serves as a visual reference for rotation. The second component G2 is visible on the back.

Some details of the surgical guide 1 briefly described above are described hereinafter. Connection Sff defines, together with the arch structure Ar associated thereto, a stirrup solidly associated with the main attachment portion Gd. Since connection Sff defines a right angle, the arch structure Ar lies on a plane substantially perpendicular to that of the main attachment portion Gd. When the surgical guide is implanted on the bony site, the main attachment portion Gd extends on a front plane parallel to the axis of femur Fe, whereas the arch structure extends beyond the distal end Ed according to a plane orthogonal to the axis of femur Fe.

Appendix 10 extends along the symmetry axis of the arch structure Ar. Pin 12 arranged at the end thereof is placed substantially at the center of the arch and is designed for aligning with the longitudinal axis of femur Fe. Thus, the hinging axis of template Gr substantially coincides with the longitudinal axis of femur Fe. It should be noted that while the above hinging allows a rotational degree of freedom to template Gr, it remains in any case constrained to the arch structure Ar.

Template Gr is designed for guiding a marking operation of the distal epiphyseal end Ed of femur Fe. In particular, it has four guiding holes 19 intended for guiding a dedicated instrument in perforating the distal face of femur Fe. From the following description of the operative technique associated with the device it is seen that the holes made with the instrument then define the position and the orientation of the implanted knee prosthesis.

The dual line 18 that allows as reference position to be determined for template Gr has been mentioned above. In the reference position (corresponding to the alignment of the dual line 18), template Gr is symmetrically oriented relative to the axis defined by appendix 10. It should be noted that such reference position corresponds to the orientation of the knee prosthesis planned in the preoperative stage.

It should also be noted that the hinging constraint between template Gr and arch structure Ar has a predetermined friction, so a certain torsional resistance is opposed to the movement of template Gr. The rotations of template Gr, given the shape thereof, are limited by the interference with the arch structure Ar. In particular, the angular range allowed to the template is always less than 20°, and preferably less than 15°.

Slot SLO of template Gr is a through slit perpendicular to the symmetry axis of template Gr; it is obtained underneath the hinging point with appendix 10.

The main attachment portion Gd has a slit 11, oriented parallel to the lying plane of the arch structure Ar and of template Gr, which defines a resection guide for making the distal cut Td defined above. Two of the four supports B that couple with shape constraint with femur Fe are arranged in the proximity of a proximal edge of the main attachment portion Gd. The remaining two supports B, on the other hand, are arranged on as many secondary attachment portions Ga, defined by two opposite arms that branch off, at a right angle, from the ends of the arch structure Ar.

The four supports B described above, as it shall appear in more detail in the description below, allow the first component G1 of the surgical guide 1 to be uniquely coupled with the distal end Ed of the patient's femur Fe. In fact, it should be noted that such first component G1, in particular in its attachment portions Gd, Ga, is designed based on CT images of the patient's bony site acquired in the preoperative stage. In other words, the surgical guide is patient specific.

The secondary attachment portions Ga develop opposite to each other and are designed for associating respectively with the medial and lateral epicondyle of femur Fe. The main attachment portion Gd, on the other hand, associates with the front face of the distal end Ed of femur Fe.

In the proximity of supports B there are provided fixing holes 22, 23 intended for introducing the fixing nails 15, 16, 17 mentioned above. Two fixing holes 22 skewed with respect to each other are provided on both secondary attachment portions Ga. On the other hand, two parallel fixing holes 23 normal to the portion plane are provided on the main attachment portion Gd, in the proximity of each one of supports B; two additional fixing holes 24, again parallel to the others, are arranged on the distal edge of the main attachment portion Gd. The second component G2 of the surgical guide 1 has a fork structure, defined by a grip 21 wherefrom a coupling portion 20 to the femoral epiphyseal end and a tab SLO' designed for inserting into slot SLO described above branch off, respectively. The coupling portion 20 has a planar U shape intended for solidly coupling (for example by screws) with the proximal end Ep of tibia Ti; in particular, it abuts on a flat surface obtained by a preliminary tibial cut Tt of the bone. The coupling portion 20 and tab SLO' are parallel to each other.

FIGS. 5-10 show an embodiment version 1' of the surgical guide according to the present invention. In the description of this version, components and features similar to those of the version discussed above shall be identified by the same reference numeral. Also the surgical guide 1' according to this version comprises a first component G1' uniquely coupled with the end of femur Fe, a template Gr' rotatable with respect to the first component G1' and a second component G2 for coupling template Gr' with the proximal end Ep of tibia Ti.

The structure of the first component G1', however, is slightly modified compared to the first embodiment version. In particular, the arch structure Ar whereon template Gr is hinged is here replaced by an attachment plate Pi. It should be noted that the attachment plate Pi has smaller dimensions than the arch structure Ar proposed in the previous version. The modification made advantageously allows the patient's leg to be extended during the operation; in the first embodiment version, the dimensions in side direction of the arch structure Ar prevent such operation.

The attachment plate Pi is connected by means of a connection Sff to a main attachment portion Gd. Connection Sff and attachment portion Gd are totally similar to those described above, except for the fact that the attachment portion Gd comprises a seventh fixing hole 25, skewed with respect to the six ones already provided in the first embodiment version.

On the contrary, the second embodiment version is not provided with the secondary attachment portions Ga. This is due to it being provided with two distal fixing holes DFH directly onto the attachment plate Pi, which among the other things is designed for resting against the bony site defining the unique coupling of the first component G1'.

Figure 8:
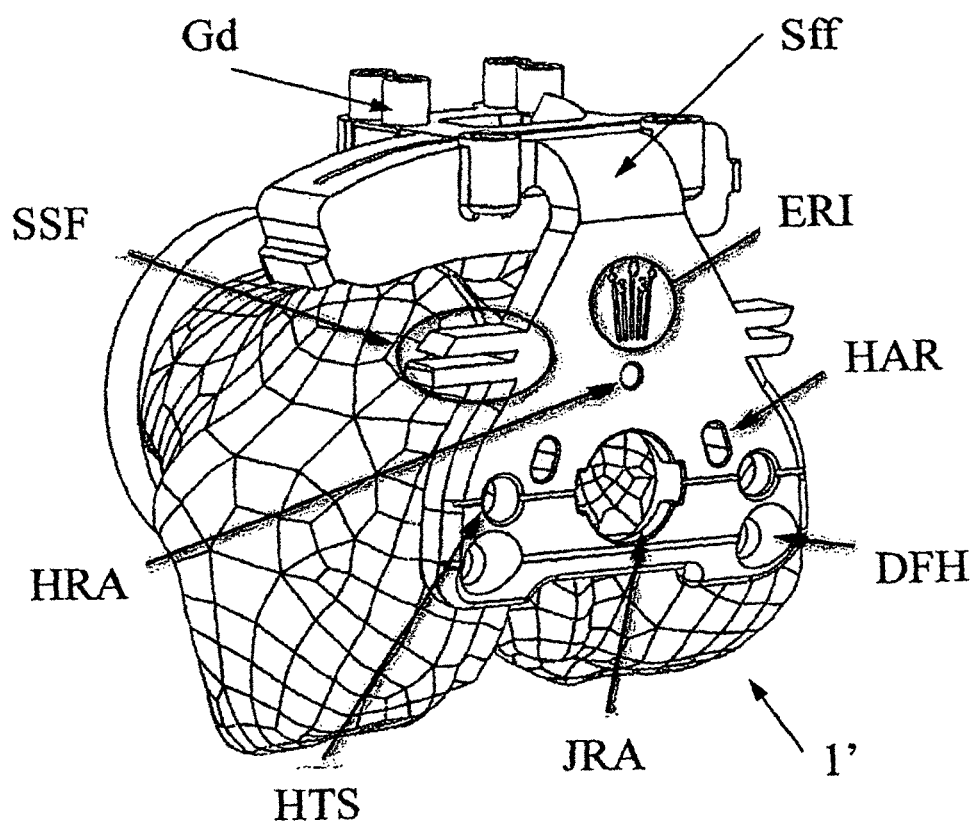
Figure 9:
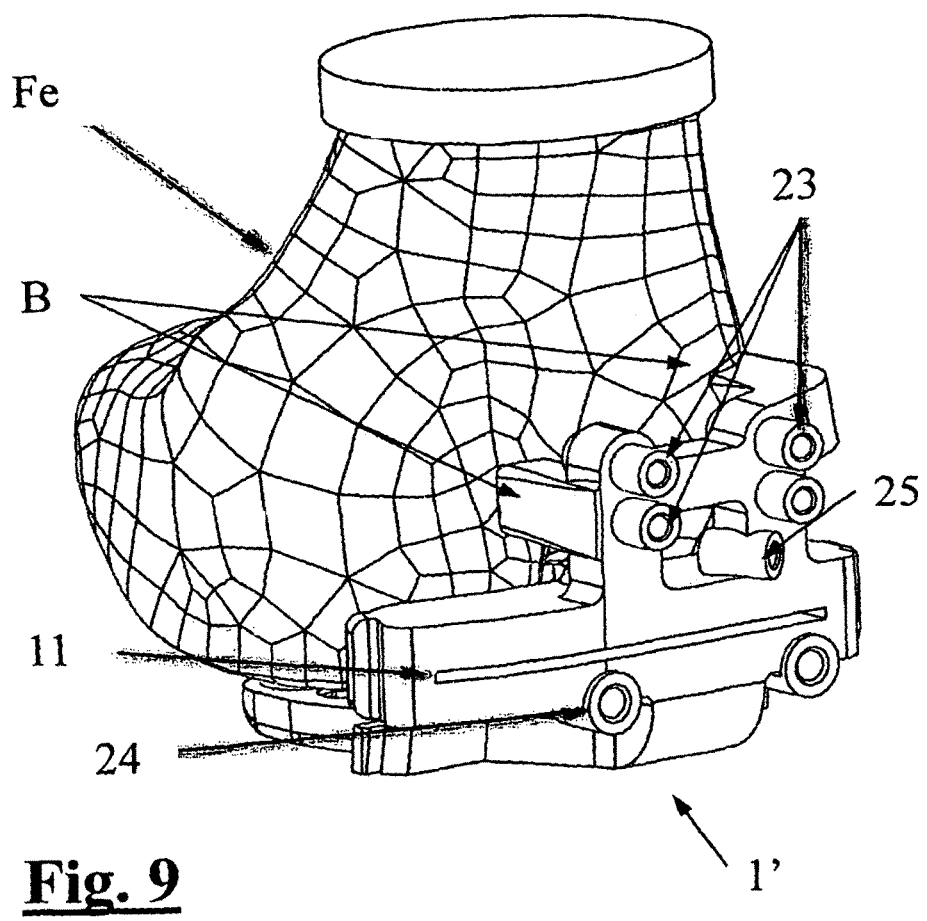
FIG. 9 shows a perspective view of a detail of the surgical guide of FIG. 6.

The attachment plate Pi, visible in FIG. 8 without the other elements associated thereto, has a substantially triangular shape. Distal fixing holes DFH are provided at the vertices of the base of such triangle; two coupling holes HTS for a shim are made a little above. In a central position at the height of the coupling holes HTS, substantially aligned with the longitudinal axis of femur Fe, there is provided a circular seat JRA wherein a button (not visible in the figures) of template Gr' rotatably couples. Template Gr' therefore is partly overlapped on plate Pi and rotatably constrained thereto.

Template Gr' has a polygonal geometry, in particular pentagonal. Slot SLO is provided at a base of the pentagon, similar to that described with reference to the previous version; at the three remaining vertices of the triangle there are obtained as many holes. The hole opposite slot SLO is a locking hole HFR that at a reference position of template Gr' aligns with a corresponding locking hole HRA of plate Pi.

The other two holes, symmetrically arranged with respect to an axis of template Gr', are guiding holes 19 similar to those already described with reference to the first version. Along the whole angular range of the device, they are always overlapping corresponding through slots HAR made on the plate, so that the perforating instrument can reach the underlying bony site.

There are provided two system for visually signaling the angular position of template Gr' with respect to the plate. A dual line 18' is provided in the first place, i.e. a straight line segment visible on template Gr' that aligns with a corresponding straight line segment provided on plate Pi when the template is in reference position. A goniometric scale ERI is provided in the second place on plate Gr' which cooperates with a pointer obtained on template Gr', at the vertex opposite slot SLO.

Figure 10:
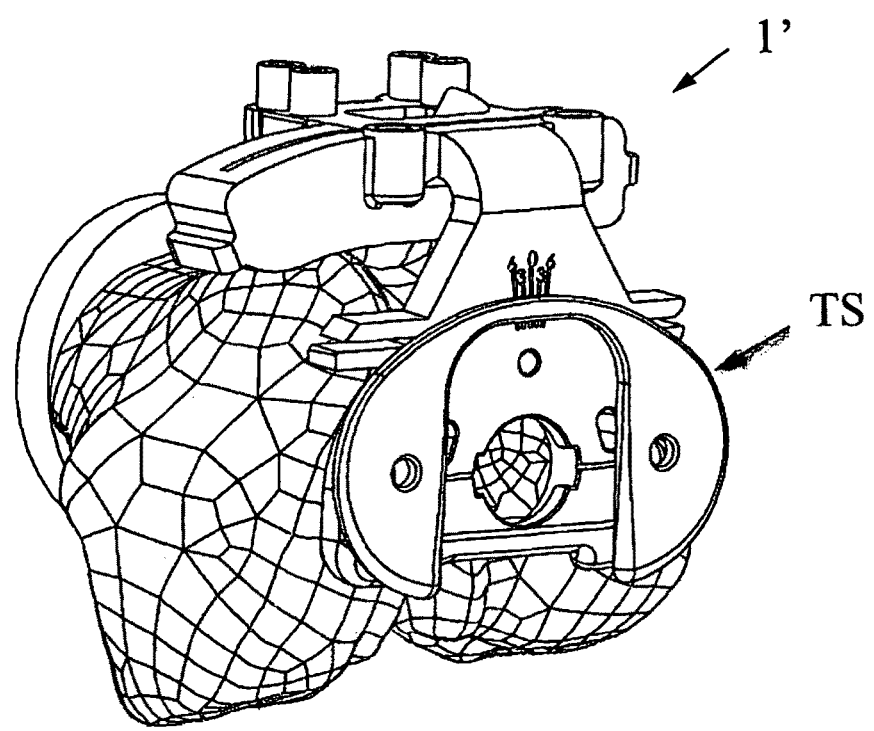

A further feature of plate Pi consists of slotted appendices SSF which define a visual reference aligned with a front plane tangent to the femur. Lastly, there is the possibility of arranging a correction shim TS between plate Pi and template Gr', coupled to plate Pi by means of the above coupling holes HTS, which allows the angle of the hinging axis between the two members to be modified. Such possibility is represented in FIG. 10.

Let us now describe the operative technique for implanting a total knee prosthesis by means of a surgical guide 1, 1' of the type described above. First, a CT image of the bony site to operate is acquired. Such image allows the operation to be planned in the preoperative stage, inter alia shaping the first component G1, G1' so that it uniquely couples with the distal epiphyseal end Ed of femur Fe. Slit 11 and the guiding holes 19—with template Gr, Gr' in reference position—are positioned so as to obtain the planned knee prosthesis configuration. In the operative stage, the tibial cut Tt is first made on the proximal epiphyseal end Ep of tibia Tt. Such cut is made with the aid of a known resection guide that is not part of the present invention.

Once the tibial cut has been made, the first component G1, G1 ' is coupled with the distal epiphyseal end Ed of the femur, and then it is fixed on site by means of dedicated nails 15, 16, 17.

Once the first component G1, G1' has been fixed into position, template Gr, Gr' is connected to tibia Ti by means of the second component G2; in particular, the coupling portion 20 of the second component G2 abuts on the surface of the tibial cut Tt where it is fixed whereas tab SLO' is inserted in the dedicated slot SLO of template Gr, Gr'. At this point, tibia Ti is solidly connected with template Gr, Gr', hinged on the fixed portion of the first component G1, G1' which in turn is solidly connected with femur Fe. The surgeon then carries out the balancing operation of the joint ligaments, which may include a slight rotation of the tibia with respect to the reference position envisioned in the preoperative planning.

Once he/she has found the correct orientation of tibia Ti with respect to femur Fe, the surgeon carries out a marking of the distal epiphyseal end Ed of femur Fe for determining such configuration. In particular, through the guiding holes 19, he/she perforates the underlying bony site defining reference holes that are used in the remainder of the operation. Once the reference holes have been made, the surgeon makes the distal cut Td of femur Fe, using the resection guide defined by slit 11.

Once the distal cut Td has been made, the surgical guide 1, 1' according to the invention can be released from the bone and removed from the operation site. Further operative steps that do not involve the surgical guide 1, 1' according to the present disclosure comprise the execution of the back cut Tp of the femur and the subsequent implantation of the knee prosthesis. It is noted that the back cut Tp is carried out by a dedicated resection guide that is positioned based on the reference holes previously made on femur Fe; the upper portion of the knee prosthesis will then be fixed based on the same holes as well.

Figure 5:
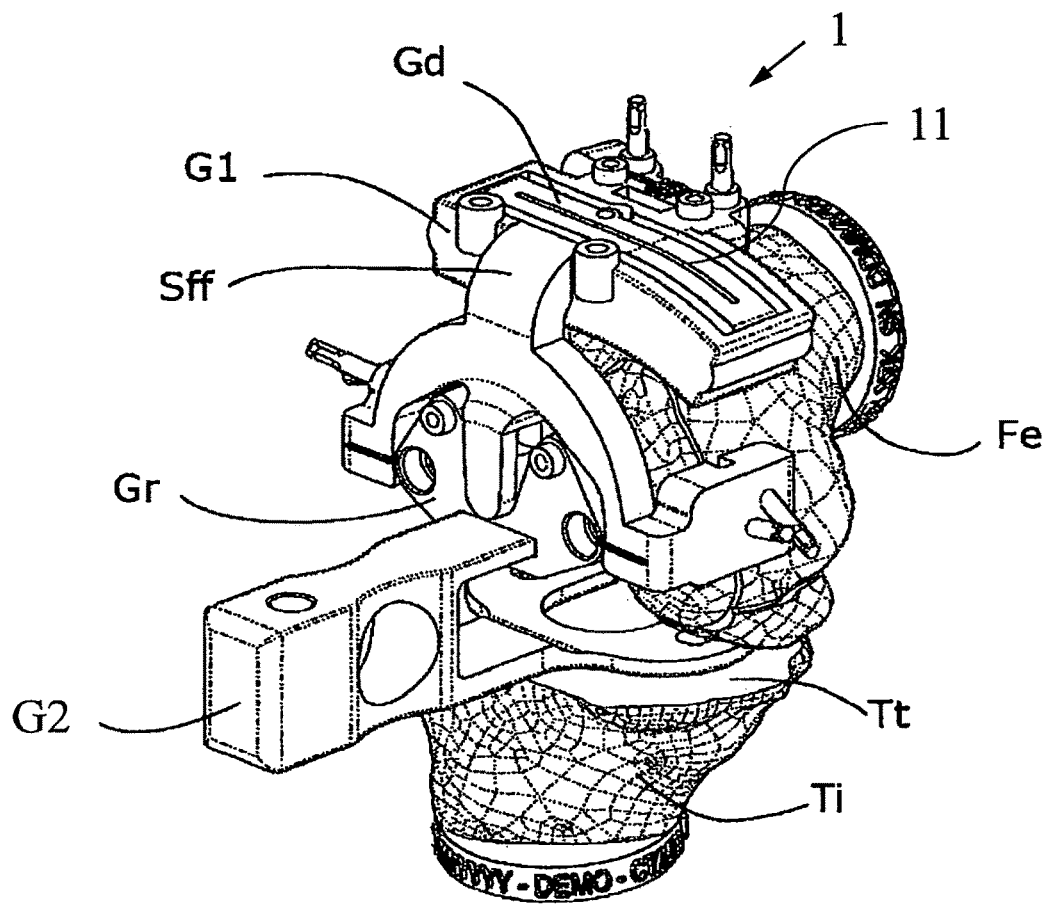
Figure 6:
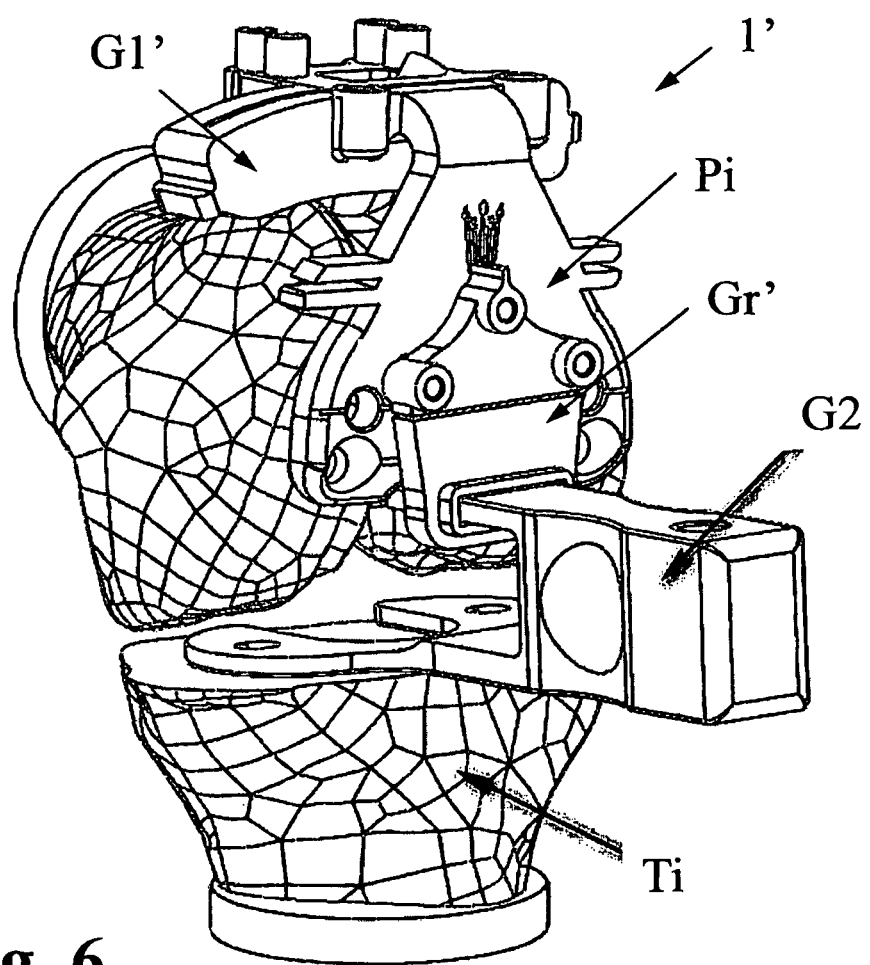
FIG. 6 shows a perspective view of a second embodiment version of the surgical guide according to the present invention, coupled with the bony site of FIG. 1.
Figure 7:
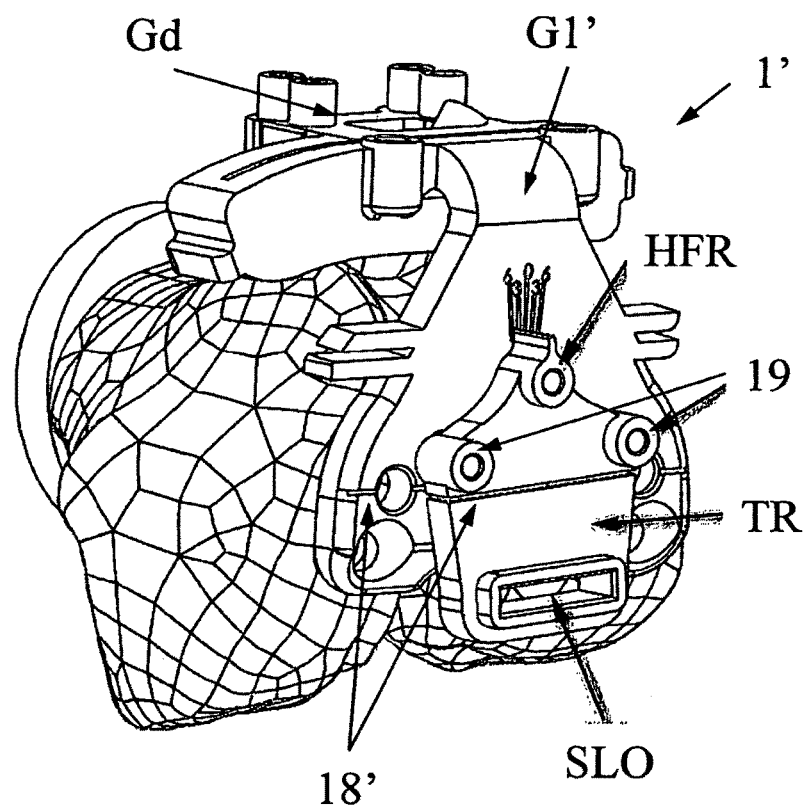
FIGS. 7-8 and 10 show perspective views of the surgical guide of FIG. 6 with some parts removed for clarity of representation.

In brief, the bony site of FIG. 1 is first prepared making the tibial cut Tt, then the first component G1, G1' is positioned on the distal end Ed of femur Fe proceeding then with fixing the subject guide with nails 15, 16 and 17. Tab SLO' of the second component (G2) is then inserted into slot SLO of template Gr, Gr' and the joint is balanced. The compacted structure is shown in FIG. 5 that does not appear to require further descriptions.

Some aspects of the second component G2, common to both embodiment versions of the surgical guide 1, 1' described above are noted below. Typically, the second component G2 herein consists of two gripper portions with two overlapping tabs, the upper one whereof (FIG. 2) has the tab SLO' at the free end thereof for penetrating slot SLO obtained in the polygonal body of template Gr (FIG. 4). The other underlying tab (FIG. 2) ends with the coupling portion 20, preferably but not necessarily shaped as a horseshoe, which inserts as in FIG. 5 as an intermediate element between cut Tt of tibia Ti and femur Fe. Characteristically, the pseudo horseshoe body shape offers a better coupling between tibia and femur and therefore allows maximizing the transmission of the force states on the tibia plate. Also the function of inserting tab SLO' into slot SLO and rotating template Gr are more convenient and effective. Lastly, we should note the advantages of the invention especially as regards the mini invasiveness that also allows greater visibility of the bone which in turn prevents rough positioning errors.

Of course, modifications, replacements and the like may be made to the invention which, being clear to the man skilled in the art, are deemed to be falling within the scope and the objects of the present disclosure.

The invention claimed is:

1. A surgical guide for implanting a knee prosthesis, the surgical guide comprising:
   a first component intended for coupling with a distal epiphyseal end of a femur and comprising
      at least one attachment portion configured to be fixed to the distal epiphyseal end of the femur, and
      an attachment plate having a substantially triangular shape and comprising a connection to said at least one attachment portion configured to be adjacent to the distal epiphyseal end of the femur;
   a template configured to guide a marking operation of the distal epiphyseal end of the femur to determine a position of the knee prosthesis;
   said template configured to be rotatably mounted relative to said first component, and comprising a slot perpendicular to a symmetry axis of said template; and
   a second component configured to couple said template with a proximal epiphyseal end of a tibia corresponding to the distal epiphyseal end of the femur;
   said second component comprising
      a grip,
      a coupling portion extending from said grip and towards said template for placement adjacent the distal epiphyseal end of the femur, and
      a tab being parallel to said coupling portion and extending from said grip, said tab configured to be inserted into said slot.

2. The surgical guide according to claim 1, wherein a relative axis of rotation between said template and said first component longitudinally crosses the femur.

3. The surgical guide according to claim 1, wherein said template is configured to rotate with respect to said first component within an angular range being between 0° and 20°.

4. The surgical guide according to claim 1, wherein said template is configured to rotate with respect to said first component within an angular range being between 0° and 15°.

5. The surgical guide according to claim 1, wherein said first component comprises a guide configured to receive a cutting tool to make a distal cut orthogonal to a longitudinal axis of the femur; and wherein said guide is configured to shift in a proximal-distal direction to make corrections on a femoral resection.

6. The surgical guide according to claim 1, wherein said first component comprises at least one support configured to couple said first component with the distal epiphyseal end of the femur.

7. The surgical guide according to claim 1, further comprising a plurality of visual indicators configured to indicate a reference position of said template with respect to said first component, the reference position reflecting an ideal orientation of the knee prosthesis.

8. The surgical guide according to claim 7, wherein said plurality of visual indicators comprises at least one goniometric scale.

9. The surgical guide according to claim 1, wherein said template comprises a plurality of guiding holes configured to guide an instrument in perforating the distal epiphyseal end of the femur.

10. A surgical guide for implanting a knee prosthesis, the surgical guide comprising:
a first component intended for coupling with a distal epiphyseal end of a femur;
a template configured to guide a marking operation of the distal epiphyseal end of the femur to determine a position of the knee prosthesis;
said template configured to be rotatably mounted relative to said first component, and comprising a slot perpendicular to a symmetry axis of said template; and
a second component configured to couple said template with a proximal epiphyseal end of a tibia corresponding to the femur;
said second component comprising
a grip,
a coupling portion extending from said grip and towards said template for placement adjacent the distal epiphyseal end of the femur, and
a tab being parallel to said coupling portion and extending from said grip, said tab configured to be inserted into said slot, said coupling portion comprising first and second arms extending from said grip and towards said template for placement adjacent the distal epiphyseal end of the femur.

11. The surgical guide according to claim 10, wherein a relative axis of rotation between said template and said first component longitudinally crosses the femur.

12. The surgical guide according to claim 10, wherein said template is configured to rotate with respect to said first component within an angular range being between 0° and 20°.

13. The surgical guide according to claim 10, wherein said template is configured to rotate with respect to said first component within an angular range being between 0° and 15°.

14. The surgical guide according to claim 10, wherein said first component comprises a guide configured to receive a cutting tool to make a distal cut orthogonal to a longitudinal axis of the femur; and wherein said guide is configured to shift in a proximal-distal direction to make corrections on a femoral resection.

15. A surgical guide for implanting a knee prosthesis, the surgical guide comprising:
a first component intended for coupling with a distal epiphyseal end of a femur;
a template configured to guide a marking operation of the distal epiphyseal end of the femur to determine a position of the knee prosthesis;
said template configured to be rotatably mounted relative to said first component, and comprising a slot perpendicular to a symmetry axis of said template; and
a second component configured to couple said template with a proximal epiphyseal end of a tibia corresponding to the femur;
said second component comprising
a grip,
a coupling portion extending from said grip and towards said template for placement adjacent the distal epiphyseal end of the femur, and
a tab being parallel to said coupling portion and extending from said grip, said tab configured to be inserted into said slot, said second component comprising an integral single piece.

16. The surgical guide according to claim 15, wherein a relative axis of rotation between said template and said first component longitudinally crosses the femur.

17. The surgical guide according to claim 15, wherein said template is configured to rotate with respect to said first component within an angular range being between 0° and 20°.

18. The surgical guide according to claim 15, wherein said template is configured to rotate with respect to said first component within an angular range being between 0° and 15°.

19. The surgical guide according to claim 15, wherein said first component comprises a guide configured to receive a cutting tool to make a distal cut orthogonal to a longitudinal axis of the femur; and wherein said guide is configured to shift in a proximal-distal direction to make corrections on a femoral resection.

20. A surgical guide for implanting a knee prosthesis, the surgical guide comprising:
a first component intended for coupling with a distal epiphyseal end of a femur;
a template configured to guide a marking operation of the distal epiphyseal end of the femur to determine a position of the knee prosthesis;
said template configured to be rotatably mounted relative to said first component, and comprising a slot perpendicular to a symmetry axis of said template; and
a second component configured to couple said template with a proximal epiphyseal end of a tibia corresponding to the femur;
said second component comprising
a grip,
a coupling portion extending from said grip and towards said template for placement adjacent the distal epiphyseal end of the femur, and
a tab being parallel to said coupling portion and extending from said grip, said tab configured to be inserted into said slot, said grip being between said coupling portion and said tab.

21. The surgical guide according to claim 20, wherein a relative axis of rotation between said template and said first component longitudinally crosses the femur.

22. The surgical guide according to claim 20, wherein said template is configured to rotate with respect to said first component within an angular range being between 0° and 20°.

23. The surgical guide according to claim 20, wherein said template is configured to rotate with respect to said first component within an angular range being between 0° and 15°.

24. The surgical guide according to claim 20, wherein said first component comprises a guide configured to receive a cutting tool to make a distal cut orthogonal to a longitudinal axis of the femur; and wherein said guide is configured to shift in a proximal-distal direction to make corrections on a femoral resection.

* * * * *